(12) United States Patent
Lee et al.

(10) Patent No.: US 6,533,741 B1
(45) Date of Patent: Mar. 18, 2003

(54) ARTICULATED UPPER EXTREMITY SPLINT TO IMMOBILIZE AND SUPPORT AN INJURED LIMB

(76) Inventors: Roger W. Lee, 9533 Sunnyside Ave., Ben Lomond, CA (US) 95005; Paul J. Martin, 1100 Clearview Dr., Hollister, CA (US) 95023

( * ) Notice: Subject to any disclaimer, the term of this patent is extended or adjusted under 35 U.S.C. 154(b) by 0 days.

(21) Appl. No.: 09/478,417

(22) Filed: Jan. 6, 2000

(51) Int. Cl.$^7$ .............................. A61F 5/00; A61F 13/00
(52) U.S. Cl. ............................ 602/20; 602/16; 602/4; 128/878
(58) Field of Search .................................. 602/5, 20–21, 602/23, 16, 4; 128/878–879, 845

(56) References Cited

U.S. PATENT DOCUMENTS

| | | | |
|---|---|---|---|
| 504,218 A | * | 8/1893 | Hoppe |
| 1,340,630 A | * | 5/1920 | Maddox |
| 1,639,815 A | * | 8/1927 | Siebrandt |
| 4,320,747 A | * | 3/1982 | Daniell, Jr. ................... 128/80 |
| 4,419,991 A | | 12/1983 | Lee ............................... 128/88 |
| 4,508,111 A | | 4/1985 | Hepburn ....................... 128/87 |
| 4,947,835 A | | 8/1990 | Hepburn et al. ........... 128/84 R |
| 5,046,488 A | * | 9/1991 | Schiek, Sr. ................... 602/19 |
| 5,232,435 A | | 8/1993 | Leibinsohn .................. 602/16 |
| 5,312,322 A | | 5/1994 | Santana ........................ 602/20 |
| 5,342,288 A | | 8/1994 | Lee et al. ....................... 602/5 |
| 5,358,469 A | | 10/1994 | Patchel et al. ................. 602/5 |
| 5,383,844 A | * | 1/1995 | Munoz et al. ................ 602/54 |
| 5,407,420 A | * | 4/1995 | Bastyr et al. ................... 602/5 |
| 5,873,847 A | | 2/1999 | Bennet et al. ................ 602/16 |

OTHER PUBLICATIONS

Publication by Reel Research And Development, Inc. published during the year 1989 and illustrating the Reel Splint 880 Series, manufactured and sold during the year 1988.

* cited by examiner

Primary Examiner—Denise M. Pothier
(74) Attorney, Agent, or Firm—Intellectual Property Law Group LLP; Otto O. Lee; Juneko C. Jackson (57) ABSTRACT

An articulated upper extremity splint for immobilizing and supporting an injured upper extremity. The splint includes a frame. The frame includes a proximal support section and a distal support section. Interconnecting the confronting ends of the proximal support section and the distal support section is a connector. The connector provides multi-directional movement for the proximal support section and the distal support section, respectively. The proximal support section and the distal support section include respective extensible support rods. The support rods are telescopically received by respective tubes of the proximal support section and the distal support section. The rods are releasably secured to the associate tubes for adjusting, respectively, the length of the proximal support section and the distal support section. Through this arrangement, the articulated upper extremity splint provides flexion and extension movements with medial and lateral side movements to the distal support section and the proximal support section, respectively.

10 Claims, 7 Drawing Sheets

ARTICULATED UPPER EXTREMITY SPLINT TO IMMOBILIZE AND SUPPORT AN INJURED LIMB

BACKGROUND OF THE INVENTION

The present invention relates in general to splints and, more particularly, to an articulated splint to immobilize and support an upper extremity human limb.

Heretofore, upper extremity splints did not provide like articulation to a complexly injured elbow joint. The articulated splints heretofore employed did not provide support members that had respective extensible and rotatable movement to accommodate a pronated or supinated upper extremity limb. Further, the articulated upper extremity splints did not provide an adjustable sling and shoulder pad attachment at opposite ends of the splint nor did they provide a positive hand grip and wrist support.

In the U.S. patent to Lee, U.S. Pat. No. 4,419,991, granted on Dec. 13, 1983, for a Splint, there is disclosed a splint that includes a frame. The frame comprises upper and lower limb support sections pivotally and rotatably interconnected. The support sections are interconnected so that one section can be adjusted to a position inclined upwardlly or downwardly relative to the other section, or can be moved to a position extending laterally at an angle away from the other section, or can be adjusted to a position involving up, down and lateral movement of the sections for the purpose of angulated limb section. Each section includes parallel side members. Each side member includes a rod telescopically received by a tube. A cylindrical nut is threaded on the threaded end of each of the tubes and is arranged to releasably press the tube into frictional engagement with the associated rod for adjusting independently the length of each side member.

The patent to Lee et al., U.S. Pat. No. 5,342,288, issued on Aug. 30, 1994, for Traction Splint, discloses a traction splint for a long bone extremity fracture in which the traction splint includes a frame. The length of the frame and an angle of an ischial pad of the traction splint relative to the frame are adjusted simultaneously. The frame includes side members. Each side member includes parallel rods. The parallel rods are telescopically received by respective tubes of the side members. By retracting and extending the rods into the tubes, respectively, the extent of the respective rods are adjustable. For releasably securing the tubes, respectively, in selected positions relative to the rods, lock nuts are provided. The inner wall of each of the lock nuts is threaded. The ends of the tubes facing the rods, respectively, are formed with external threads and are received, respectively, by the internally threaded nuts. Disposed within each of the bores of the lock nuts are temporarily yieldable collets. A tight releasable locking engagement is provided between the rods and the tubes, respectively, for maintaining the adjusted length of the traction splint.

Reel Research And Development, Inc. of Ben Lomond, Calif., during the year 1982 manufactured and sold The Reel Splint pediatric articulated traction splint, Reel Splint 8800 Series. The Reel Splint pediatric articulated traction splint has been used as an upper extremity traction splint and includes a frame. The frame comprises upper and lower limb support sections pivotally and rotatably interconnected. The support sections are interconnected so that one support section can be adjusted relative to the other support section upwardly and downwardly, or can be moved to a position extending laterally or at an angle away from the other support section. Each support section includes parallel rods. The parallel rods are telescopically received by tubes, respectively, for adjusting respectively the length at which each parallel rod extends outwardly from the associated tube. Lock nuts, respectively, releasably secure the rods in the adjusted positions to the associated tubes.

In the patent to Maddox, U.S. Pat. No. 1,340,630, issued on May 18, 1920, for an Arm Abduction Splint, there is disclosed a splint for an injured arm. The splint includes a support frame to retain an injured arm in a desired position. The frame comprises rods that are pivotally and rotatably moved relative to one another and are releasably secured in the adjusted position. Trough-shaped plates are adjustably movable on the associated rods in the axial direction thereof and are releasably secured in the adjusted position.

The patent to Santana, U.S. Pat. No. 5,312,322, issued on May 17, 1994, for Three Point Extension Splint To Treat Flexion Contractures About Limb Synovial Hinge Joints, discloses a three point extension splint for correcting a flexion contracture about a limb synovial hinge joint. The three point extension splint comprises a proximal contact member for contacting the proximal section of an extremity above the flexion crease of a synovial hinge joint and a distal contact member for contacting the distal section of an extremity below the flexion crease of the synovial hinge joint. A resilient hinge joins the proximal contact member and the distal contact member. A cupping member forms the posterior assembly. Adjustable releasable straps join the bridge to the cupping member and secure the cupping member to the synovial hinge joint. Adjustable releasable straps secure the proximal contact member and the distal contact hinge member to the proximal section of the extremity above the flexure crease of the synovial hinge joint and below the flexure crease of the synovial hinge joint, respectively.

SUMMARY OF THE INVENTION

An object of the present invention is to provide an articulated upper extremity splint in which there are flexion and extension movements in conjunction with medial and lateral side movements of the opposing ends of the splint, respectively.

Another object of the present invention is to provide an articulated upper extremity splint which adjustably conforms to the contour of an injured limb and provides secure fixation and support for the injured limb, thereby minimizing the potential for further injury to the limb.

Another object of the present invention is to provide an articulated upper extremity splint arranged to accommodate pronated and supinated injuries to the limb.

Another object of the present invention is to provide an articulated upper extremity splint that is adjustable to flex at the elbow and is positioned medially and laterally on opposing sides.

Another object of the present invention is to provide an articulated upper extremity splint in which there are extensible limb support members located at opposite ends of the splint, which extensible limb support members rotate to accommodate pronation and supination of an injured limb.

An articulated upper extremity splint for immobilizing and supporting an injured upper extremity. The splint includes a frame. The frame includes a proximal support section and a distal support section. Interconnecting the confronting ends of the proximal support section and the distal support section is a connector. The connector provides multi-directional movement for the proximal support section and the distal support section, respectively. The proximal support section and the distal support section include a respective extensible support rod. The support rods are telescopically received by respective tubes of the proximal support section and the distal support section. The rods are releasably secured to the associate tubes for adjusting, respectively, the length of the proximal support section and the distal support section. Through this arrangement, the articulated upper extremity splint provides flexion and extension movements with medial and lateral side movements to the distal support section and the proximal support section, respectively. Secured to the proximal support section and the distal support section, respectively, are upper extremity support troughs. At the free end of the distal support section is a suitable hand grip. Joined to the free ends of the distal support section and the proximal support section is a sling and a shoulder pad.

DESCRIPTION OF THE PREFERRED EMBODIMENTS

Figure 1:
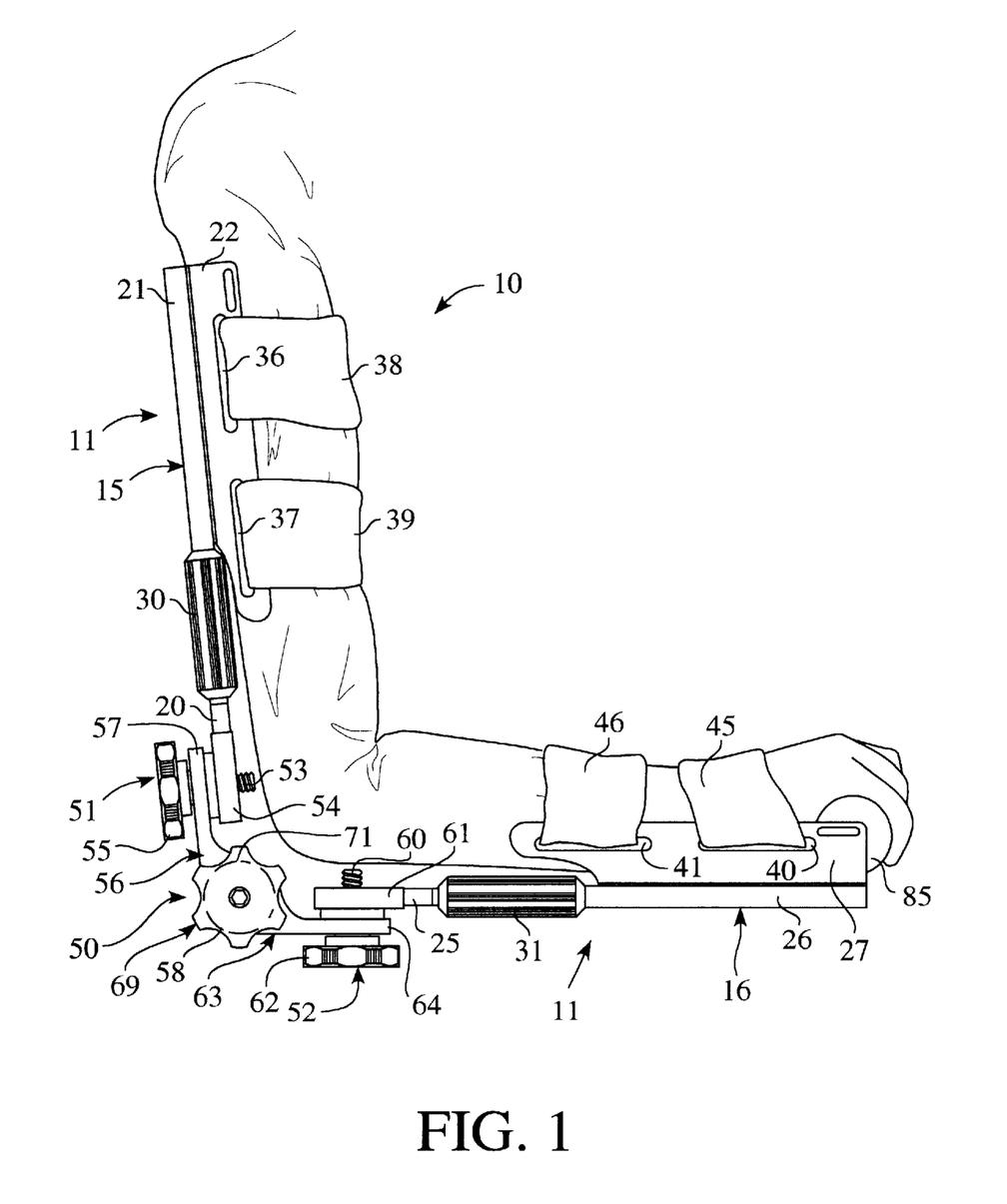
FIG. 1 is a fragmentary side elevation view of the articulated upper extremity splint embodying the present invention illustrated supporting an upper injured extremity.
Figure 2:
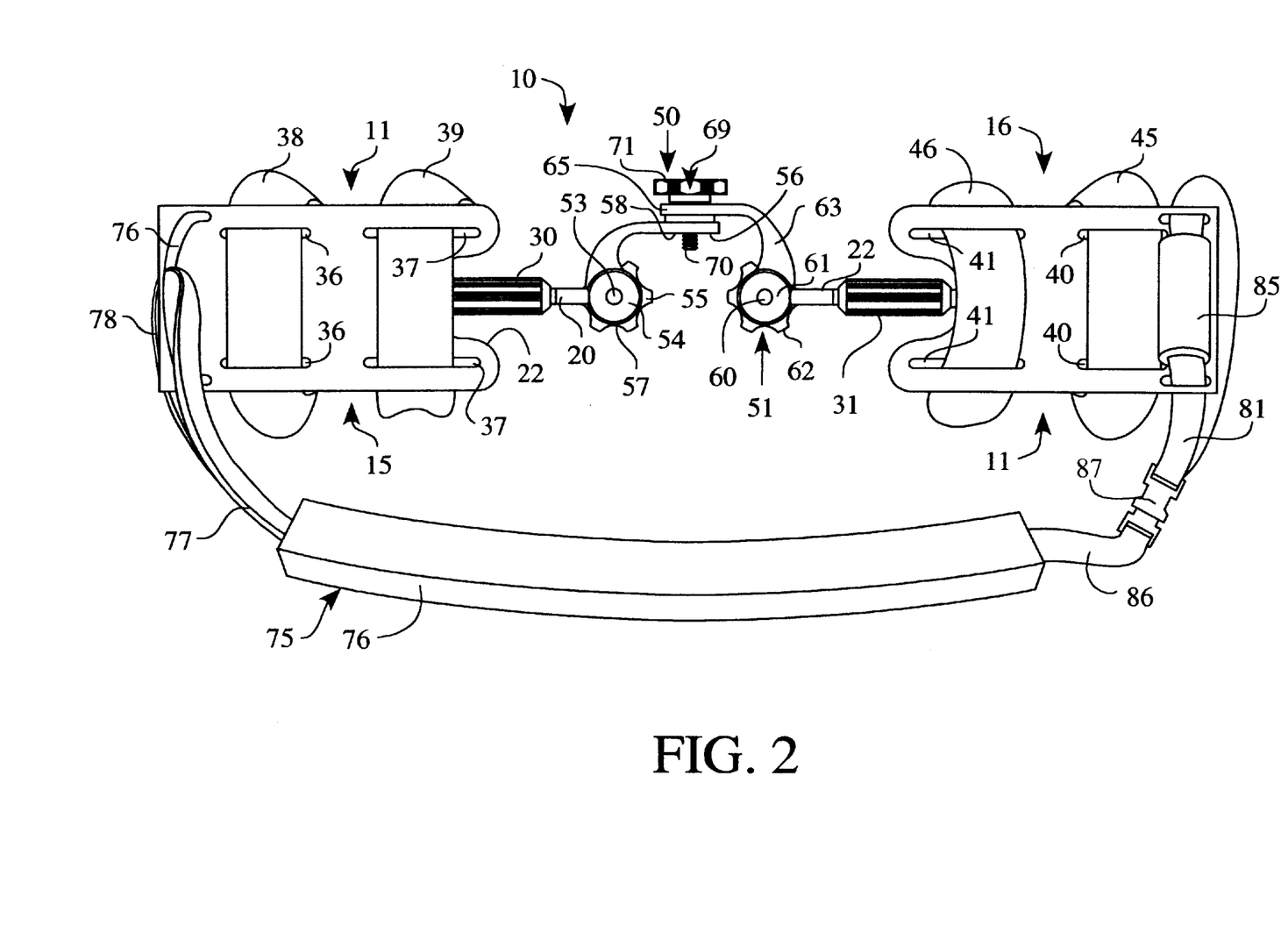
FIG. 2 is a plan view of the articulated upper extremity splint shown in FIG. 1 illustrated with the anchor straps thereof in limb securing position.
Figure 3:
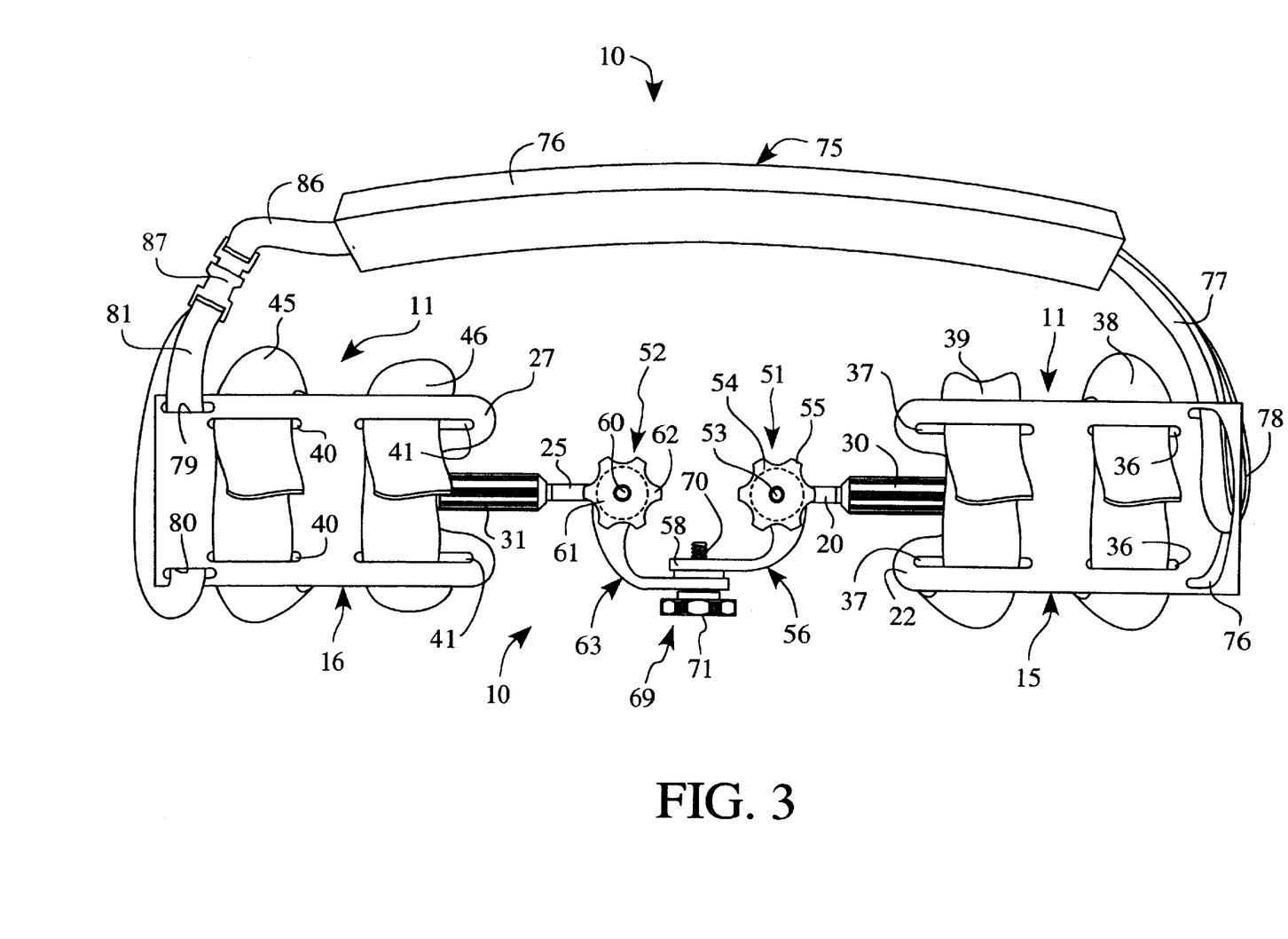
FIG. 3 is a bottom view of the articulated upper extremity splint shown in FIGS. 1 and 2 illustrated with the anchor straps thereof in a limb securing position.

Illustrated in FIGS. 1–3 is an articulated upper extremity splint 10 embodying the present invention. The splint 10 comprises a frame 11. The frame 11 includes a proximal support section 15 and a distal support section 16.

Figure 4:
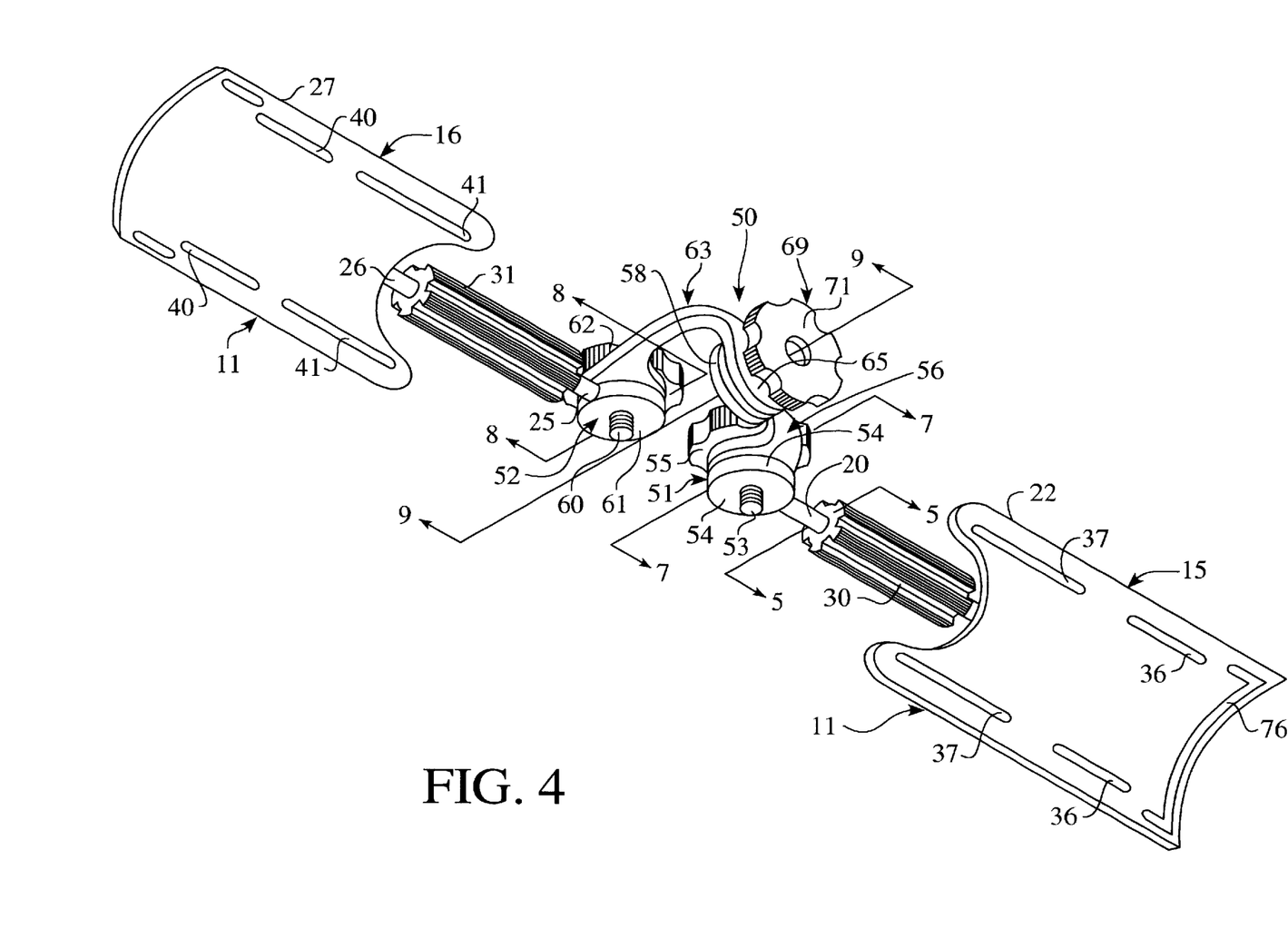
FIG. 4 is a fragmentary perspective view of the articulated upper extremity splint shown in FIGS. 1–3.

The proximal support section 15 comprises a rigid rod 20. The free end of the rod 20 is telescopically received by a rigid tube 21 (FIG. 1). Secured to the tube 21 is an upper extremity support trough 22 (FIGS. 1–4), which is suitably configured to support a human limb. In the exemplary embodiment, the trough 22 is secured to the tube 21 by welding or soldering. The rod 20 is adjustably positioned within the tube 21 and the extent of the extension of the rod 20 from the tube 21 determines the adjusted length of the proximal support section 15. In a similar manner, the distal support section 16 comprises a rigid rod 25. The free end of the rod 25 is telescopically received by a rigid tube 26 (FIGS. 1 and 4). Secured to the tube 26 is an upper extremity support trough 27 (FIGS. 1–4), which is suitably configured to support a human limb. In the exemplary embodiment, the trough 27 is secured to the tube 26 by welding or soldering. The rod 25 is adjustably positioned within the tube 26 and the extent of the extension of the rod 25 from the tube 26 determines the adjusted length of the distal support section 16. Thus, by retracting and extending the rods 20 and 25 into and out of the tubes 21 and 26, respectively, the length of the proximal support section 15 and the distal support section 16, respectively, are adjusted. Thus, the proximal support section 15 and the distal support section 16, respectively, have medial movement. The distal support section 16 should be adjusted through the rod 25 and the tube 31 to a length to accommodate distal anatomical limb length.

In the exemplary embodiment, the rods 20 and 25 are made of steel and the troughs 22 and 27 are made of aluminum. The tubes 21 and 26, in the exemplary embodiment, are made of aluminum, hard injection molded plastic, extruded hardened plastic, or other like light material.

For releasably securing the rods 20 and 25 to the tubes 21 and 26, respectively, to maintain the rods 20 and 25 in the selected positions relative to the tubes 21 and 26, respectively, suitable releasable locking devices 30 and 31 are provided (FIGS. 1–6). The locking devices 30 and 31 are similar in construction and operation. Therefore, only the locking device 31 will be illustrated and described herein in detail.

Figure 5:
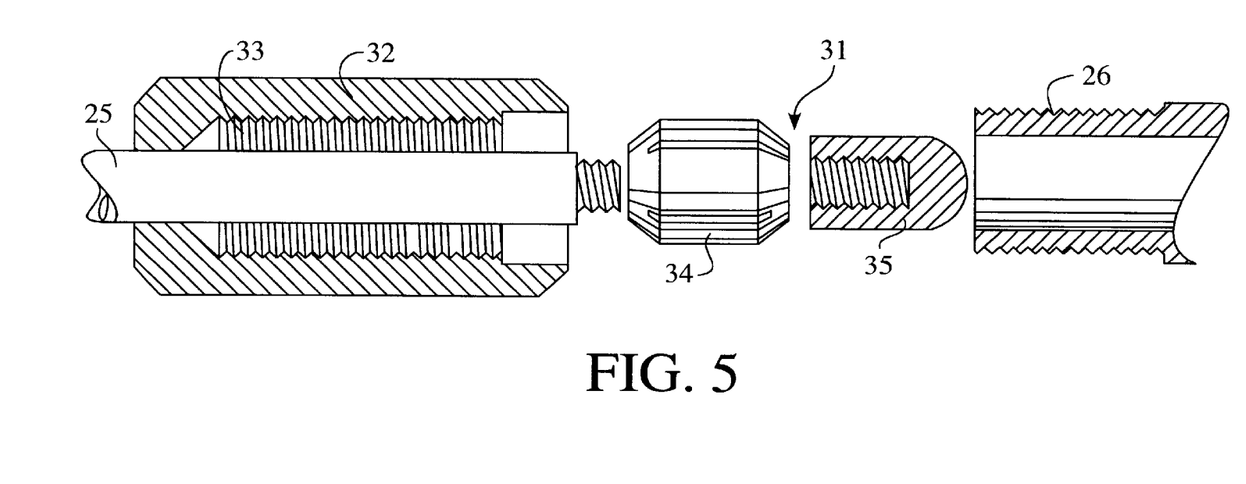
FIG. 5 is an enlarged, fragmentary, exploded axial sectional view, partially in elevation, taken along line 5—5 of FIG. 4 to illustrate a releasable locking arrangement for releasably securing telescopically received rods of the proximal support section and the distal support section, respectively.
Figure 6:
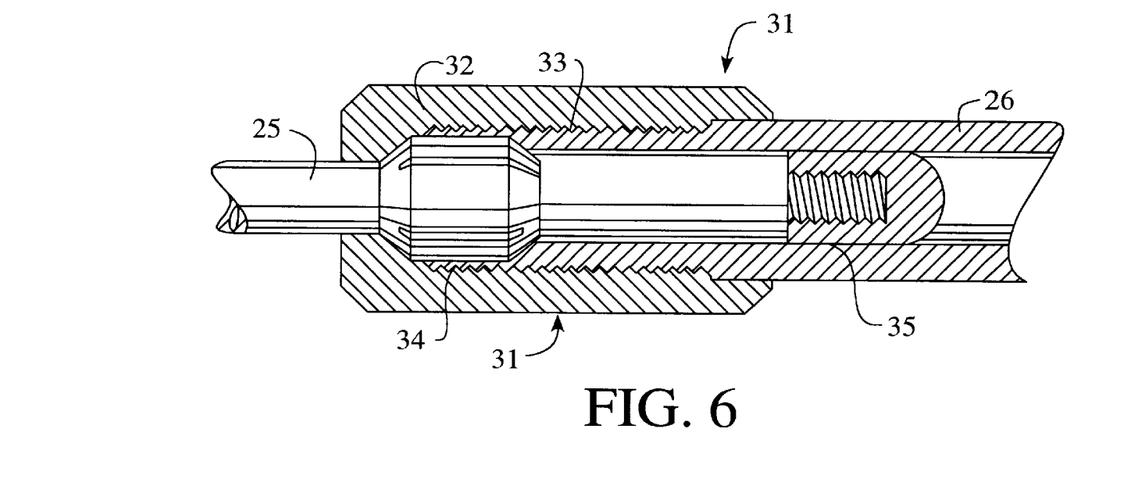
FIG. 6 is an enlarged, fragmentary, axial sectional view, partially in elevation, taken along line 5—5 of FIG. 4 to illustrate a releasable locking arrangement for releasably securing telescopically received rods of the proximal support section and the distal support section, respectively, to maintain the adjusted length of the proximal support section and the distal support section, respectively.
Figure 7:
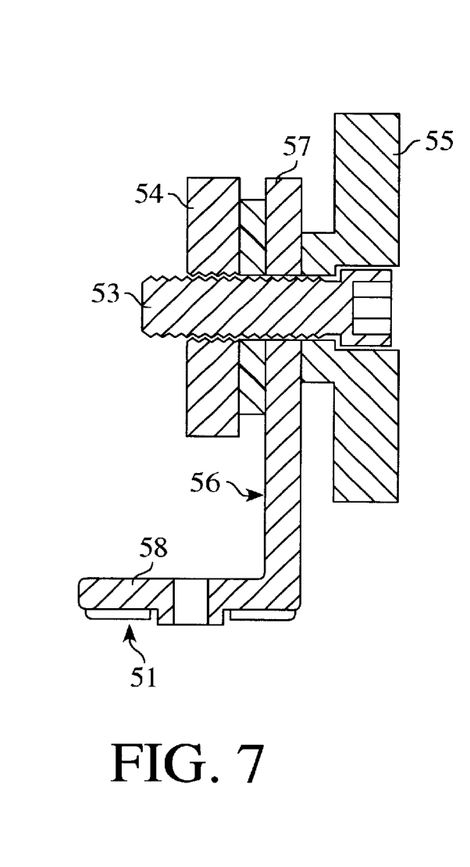
FIG. 7 is an enlarged cross-sectional view of an arrangement for adjustably rotating the proximal support section laterally taken along line 7—7 of FIG. 4.

The locking device 31 includes a cylindrically-shaped nut 32 (FIGS. 5 and 6). The nut 32 is formed with an axial bore 33. The inner wall of the nut 32 surrounding the bore 33 is threaded. The end of tube 26 facing the rod 25 is formed with external threads and is received by the bore 33 of the nut 32. Disposed within the bore 33 of the nut 32 is a temporarily yieldable collet 34. The collet 34, in the exemplary embodiment, is made of brass. At the end of the rod 25 facing the trough 27 is an internally threaded collet stop 35 with a bearing surface end to prevent the collet 34 from being removed from the rod 25. The rod 25 passes freely through the nut 32 and the collet 34 and enters the tube 26. The rod 25 is detachably secured to the collet stop 35 through threaded engagement. By rotating the nut 32 into threaded engagement with the tube 26 to move the nut 32 toward the trough 27, the collet 34 is urged toward the tube 26 and the collet 34 is temporarily compressed by the wall surrounding the bore 33 of the nut 32 until a tight releasable locking engagement is made between the rod 25 and the tube 26. The compression of the collet 34 causes the collet 34 to releasably grip the rod 25. The releasable locking devices 30 and 31 are of the type disclosed in the U.S. patent to Lee, et al., U.S. Pat. No. 5,342,288, granted on Aug. 30, 1994 for Traction Splint and is disclosed herein by reference.

In the exemplary embodiment, the trough 22 (FIGS. 1–4) is formed with a pair of transversely spaced slots 36 and a pair of transversely spaced slots 37 spaced longitudinally from the slots 36. The slots 36 receive an anchor strap 38 and the slots 37 receive an anchor strap 39. The straps 38 and 39 overlie the dorsum of an injured limb. At the ends of the straps 38 and 39 are suitable fasteners. In the exemplary embodiment, the fasteners are the well-known loop and hook type fasteners. The straps 38 and 39, when the employment thereof is desired, maintain the injured limb securely supported to the trough 22.

In a similar manner, the trough 27, in the exemplary embodiment, is formed with a pair of transversely spaced slots 40 and a pair of transversely spaced slots 41 spaced longitudinally from the slots 40. The slots 40 receive an anchor strap 45 and the slots 41 receive an anchor strap 46. The straps 45 and 46 overlie the dorsum of the injured limb. At the ends of the straps 45 and 46 are suitable fasteners. In the exemplary embodiment, the fasteners are the well-known loop and hook type fasteners. The straps 45 and 46, when the use thereof is desired, maintain the injured limb securely supported to the trough 27.

The slots 36, 37, 40 and 41 can be modified to accommodate the use of materials other than anchoring straps, such as swath material, Cling and Curlex medical binding material, or other binding material. There are times when anchoring straps, such as anchoring straps 38, 39, 45 and 46 may not be desirable. There are occasions when a swath and/or a binding material may be desired. There are times when neither straps, swathes and binding material may not be needed.

Interconnecting the proximal support section 15 and the distal support section 16 of the frame 11 is a connector or hinge 50. The connector 50 (FIGS. 1–4) provides up and down movement for the proximal support section 15 and the distal support section 16, respectively. Also, the connector 50 provides lateral movement for the proximal support section 15 and the distal support section 16, respectively.

Toward this end, the connector 50 comprises a proximal support section rotatable support 51 (FIGS. 1–4 and 7) and a distal support section rotatable support 52 (FIGS. 1–4 and 8). The rotatable support 51 includes a threaded shaft 53. Disposed in threaded engagement with the shaft 53 at one end thereof is an internally threaded annular disk 54. The axis of the disk 54 is coextensive with the axis of the shaft 53. Fixed to the disk 54 for rotation therewith is the proximal end of the rod 20. The rod 20 extends radially from the disk 54 and is perpendicular to the axis of the shaft 53. In the exemplary embodiment, the proximal support section 15 is capable of rotating 250 degrees about the axis of the shaft 53.

Figure 8:
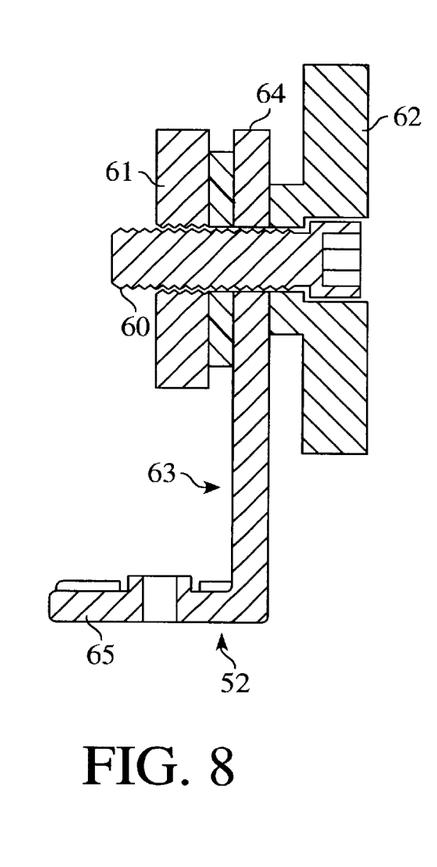
FIG. 8 is an enlarged cross-sectional view of an arrangement for adjustably rotating the distal support section laterally taken along line 8—8 of FIG. 4.

At the opposite end of the shaft 53 is fixedly secured a knob 55 for imparting rotation to the shaft 53. Mounted on the shaft 53 intermediate the disk 54 and the knob 55 is a bridging member 56 (FIGS. 1–4 and 7) that has at the opposite ends thereof rings 57 and 58 (FIG. 8). The axes of the rings 57 and 58 are angularly spaced apart by ninety degrees. The ring 57 loosely surrounds the shaft 53. The ring 58 is internally threaded. In the exemplary embodiment, a suitable washer is disposed on the shaft 53 between the disk 54 and the ring 57 of the bridging member 56. In the exemplary embodiment, the side of the ring 57 facing the washer is formed with angularly spaced gripping projections disposed generally along the periphery of the side thereof facing the washer. Through this arrangement, the proximal support section 15 can be adjustably moved laterally when the knob 55 is turned in a direction enabling the disk 54 to be rotated about the axis of the shaft 53. When the knob 55 is rotated in an opposite direction, the shaft 53 draws the disk 54 toward the knob 55 into locking engagement between the knob 55 and the ring 57 of the bridging member 56. Thus, the disk 54 is releasably locked in the adjusted position about the shaft 53.

The rotatable support 52 for the distal support section 16 includes a threaded shaft 60. Disposed in threaded engagement with the threaded shaft 60 at one end thereof is an internally threaded annular disk 61. The axis of the disk 61 is coextensive with the axis of the shaft 60. Fixed to the disk 61 for rotation therewith is the proximal end of the rod 25 (FIGS. 1–4 and 8). The rod 25 extends radially from the disk 61 and is perpendicular to the axis of the shaft 60. In the exemplary embodiment, the proximal support section 15 is capable of rotating 250 degrees about the axis of the shaft 53. In the exemplary embodiment, the distal support section 16 is capable of rotating 250 degrees about the axis of the shaft 60. In the exemplary embodiment, the angular displacement for the proximal support section 15, relative to the distal support section 16 about the axis of a shaft 70, can reach 220 degrees. In the exemplary embodiment, the angular displacement for the distal support section 16, relative to the proximal support section 15 about the axis of the shaft 70, can reach 220 degrees.

At the opposite end of the shaft 60 is fixedly secured a knob 62 for imparting rotation to the shaft 60. Mounted on the shaft 60 intermediate the disk 61 and the knob 62 is a bridging member 63 (FIGS. 1–4 and 8) that has at the opposite ends thereof rings 64 and 65 (FIG. 8). The axes of the rings 64 and 65 are angularly spaced apart by ninety degrees. The ring 64 loosely surrounds the shaft 60. The ring 65 is internally threaded. In the exemplary embodiment, a suitable washer is disposed on the shaft 60 between the disk 61 and the ring 64 of the bridging member 63. In the exemplary embodiment, the side of the ring 64 facing the washer is formed with angularly spaced gripping projections disposed generally along the periphery of the side thereof facing the washer. Through this arrangement, the distal support section 16 can be adjustably moved laterally when the knob 62 is turned in a direction enabling the disk 61 to be rotated about the axis of the shaft 60. When the knob 62 is rotated in an opposite direction, the shaft 60 draws the disk 61 toward the knob 62 into locking engagement between the knob 62 and the ring 64 of the bridging member 63. Thus, the disk 61 is releasably locked in the adjusted position about the shaft 60.

As previously stated, the connector 50 also provides up and down movement for the proximal support section 15 and the distal support section 16, respectively. Toward this end, the connector 50 (FIGS. 1–4 and 9) includes an intermediate rotatable support 69 disposed between the proximal rotatable support 51 and a distal rotatable support 52. The intermediate rotatable support 69 includes the threaded shaft 70. The shaft 70 is disposed in spaced relation to and between the shafts 53 and 60 of the proximal support section rotatable support 51 and the distal support section rotatable support 52. At one end of the shaft 70 are disposed the internally threaded rings 58 and 65 of the bridging members 56 and 63, respectively. The rings 58 and 65 are disposed in threaded engagement with the shaft 70.

Figure 9:
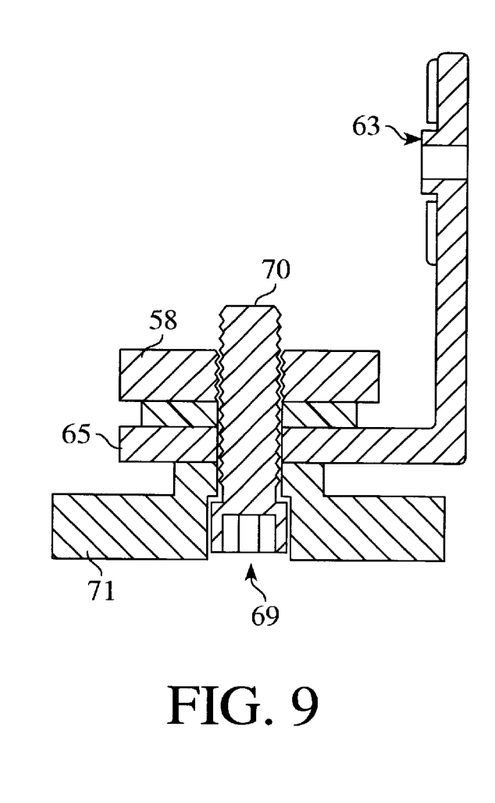
FIG. 9 is an enlarged cross-sectional view of an arrangement for adjustably rotating the proximal support section and the distal support section, respectively, for up and down movement taken along 9—9 of FIG. 4.

Fixed to the shaft 70 is a knob 71 for imparting rotation to the shaft 70. In the exemplary embodiment, between the rings 58 and 65 is disposed a suitable washer. In the exemplary embodiment, the sides of the rings 58 and 65 facing the washer therebetween are formed with locking projections. The rings 58 and 65 are oppositely threaded. By turning the knob 71 in one direction, the internally threaded rings 58 and 65 of the bridging members 58 and 63, respectively, are released from locking engagement. The rings 58 and 65 are then, respectively, rotatably movable about the axis of the shaft 70 for adjustably moving the proximal support section 15 and the distal support section 16, respectively, in the up and down direction. When the knob 71 is turned in the opposite direction, the threaded rings 58 and 65 of the bridging members 58 and 63, respectively, are locked in the set position.

Before adjusting the lateral movements of the proximal support section 15 and the distal support section 16, respectively, through the proximal rotatable support 51 and the distal rotatable support 52, respectively, the intermediate rotatable support 69 is in a locked adjusted position. After the intermediate rotatable support 69 is in the locked adjusted position, the proximal support section 15 and the distal support section 16 are set in their respective desired lateral positions. Thereupon, the knobs 62 and 71 are rotated to lock, respectively, the proximal limb support section 15 and the distal limb support section 16 in their respective desired lateral positions through the proximal rotatable support 51 and the distal rotatable support 52.

A sling 75 (FIGS. 2 and 3) with a suitable shoulder pad 76 is attached to opposite ends of the frame 11. In the exemplary embodiment, the shoulder pad 76 is made of suitable foam material enveloped by a closed cell material, such as nylon, to prevent the introduction of foreign materials into the inner foam section of the sling. In the exemplary embodiment, the contour of the pad 76 is tubular for comfort and for reducing pressure point sensitivity. The trough 22 of the proximal support section 15, in the exemplary embodiment, is formed at the free end thereof with a transversely disposed semicircular or arcuate slot 76. A suitable strap 77 is attached at one end thereof to one end of a strap 78. At the other end of the strap 78 is a loop that interconnects with the walls of the arcuate slot 76.

At the free end of the trough 27 of the distal support section 16 of the frame 11 are formed transversely spaced, longitudinally extending slots 79 and 80. A strap 81 with a suitable fastener at the end thereof, such as a well-known loop and hook type fastener, is received by the slots 79 and 80. The strap 81 carries a suitable generally transversely disposed hand grip 85 (FIGS. 1 and 2). In the exemplary embodiment, the hand grip 85 is a closed cell, extruded tubing manufactured by Rubatex Corporation of Roanoke, Va. Other foam materials can be employed, such as vinyl nitrile. The hand grip 85 is movable and adjustably positioned through the connection with the strap 81. The end of the support sling 75, opposite the end of the support sling 75 attached to the trough 22, is attached to the trough 27 through the strap 81. The interconnection between the strap 81 and the end of the support sling 75 adjacent thereto includes a suitable releasable attachment 87 (FIGS. 2 and 3) for enabling the adjustment of the length and the angle of the support sling 75. The attachment 87 has releasably attached components. One of the components has a buckle for adjusting and locking a strap 86. The strap 86 is secured to the end of the support sling 75 adjacent the strap 81.

Figure 10:
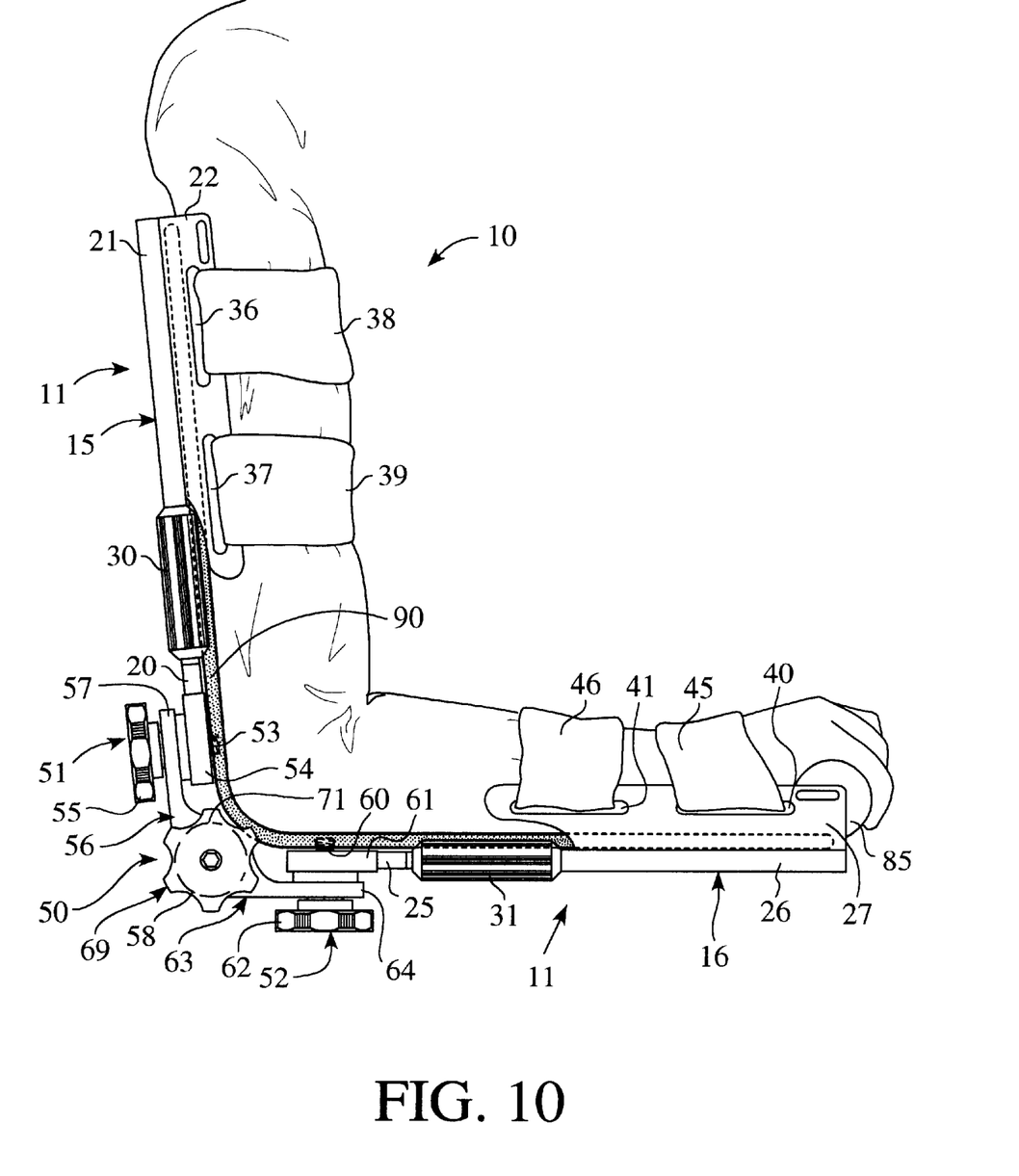
FIG. 10 is a fragmentary side elevation view of the articulated upper extremity splint illustrated in FIGS. 1–3 and shown with a pad for increasing patient comfort and for eliminating the use of adjunctive medical product padding.

Depicted in FIG. 10 is a suitable adjunctive pad 90. The pad 90 extends along the length of the proximal support section 15 and along the length of the distal support section 16. The pad 90, in the exemplary embodiment, is of a width to accommodate the trough 22 and the trough 27. In the exemplary embodiment the width of the pad 90 is approximately four and one-half inches. In the exemplary embodiment, the thickness of the pad 90 is approximately one quarter to one-half inch in length. In the exemplary embodiment, the core of the pad 90 is made of a suitable soft and padded foam material. Such foam material may be closed cell to inhibit moisture absorption. An outer closed cell material or nylon envelopes the foam material of the pad 90 to prevent the seeping of foreign substances or contaminant fluids into the core of the pad 90. The pad 90 provides alignment and support for fractures which are adjacent to the elbow of the injured person. The pad 90 increases patient comfort and eliminates the use of adjunctive medical product padding. Suitable seams, not shown, are formed in the pad 90 intermediate the ends thereof for flexure. In the exemplary embodiment, the pad 90 is freely disposed between the limb of the injured person and the support sections 15 and 16 of the frame 11.

What is claimed is:

1. An articulated upper limb splint comprising:
    (a) a frame having a proximal limb support section and a distal limb support section; and
    (b) a connector interconnecting confronting ends of said proximal limb support section and said distal limb support section,
    (c) said connector comprising:
        (1) a proximal support section rotatable support secured at one end to the proximal end of said proximal limb support section for releasably securing said proximal limb support section in an adjusted lateral position,
        (2) a distal support section rotatable support releasably secured at one end to the proximal end of said distal limb support section for releasably securing said distal limb support section in an adjusted lateral position, and
        (3) means interconnecting said proximal support section rotatable support and said distal support section rotatable support for releasably securing said proximal limb support section and said distal limb support section, respectively, in an adjusted up and down movement,
        wherein said means comprises an intermediate rotatable support, a first bridging member interconnecting said intermediate rotatable support and said proximal support section rotatable support, and a second bridging member interconnecting said intermediate rotatable support and said distal support section rotatable support, said intermediate rotatable support releasably securing said proximal limb support section and said distal limb support section, respectively, in adjusted up and down positions,
        wherein said proximal support section rotatable support includes a first threaded shaft, and wherein said distal support section rotatable support includes a second threaded shaft, and wherein said intermediate rotatable support includes a third threaded shaft, said first bridging member being formed with annular ends with the axes of the annular ends being spaced ninety degrees apart, said second bridging member being formed with annular ends with the axes thereof being spaced ninety degrees apart, said first threaded shaft being received by one annular end of said first bridging member, said third threaded shaft being received by the other annular end of said first bridging member, said second threaded shaft being received by one annular end of said second bridging member, and said third threaded shaft being received by the other annular end of said second bridging member,
        wherein said third threaded shaft is rotated in one direction enabling said annular ends of said first and third bridging members received by said third threaded shaft to be rotated freely about the axis of said third threaded shaft for adjustably positioning said proximal support section and said distal support section, respectively, in the up and down position, said third threaded shaft being rotated in an opposite direction for releasably securing said proximal support section and said distal support section in their respective adjusted up and down positions, (4) a first internally threaded first disk for receiving said first threaded shaft in threaded engagement, and a second internally threaded disk for receiving said second threaded shaft in threaded engagement, said first shaft being rotated in one direction to enable said first disk to be rotated for adjustably positioning said proximal support section laterally, said second threaded shaft being rotated in one direction to enable said second disk to be rotated for adjustably positioning said distal support section laterally, said first shaft being rotated in an opposite direction for releasably securing the proximal support section in the adjusted position, said second shaft being rotated in an opposite direction for releasably securing the distal support section in the adjusted position, (5) a first rigid rod secured to said first internally threaded disk for supporting said proximal limb support section and a second rigid rod secured to said second internally threaded disk for supporting said distal limb support section, a first rigid tube for telescopically receiving said first rigid rod for adjusting the length of said proximal limb support section, a second rigid tube for telescopically receiving said second rigid rod for adjusting the length of said distal limb support section, a first locking device for releasably securing said first rigid rod to said first rigid tube for maintaining the adjusted length of said proximal limb support section, and a second locking device for releasably securing said second rigid rod to said second rigid tube for maintaining the adjusted length of said distal limb support section.

2. An articulated upper limb splint as claimed in claim 1 and comprising a first trough secured to said first tube for engaging a limb supported by said proximal limb support section, and a second trough secured to said second tube for engaging a limb supported by said distal limb support section.

3. An articulated upper limb splint as claimed in claim 2 and comprising a hand grip, and an adjustable strap secured to opposite ends of said hand grip and attached to the distal end of said second trough for enabling said hand grip to be movable for adjustable positioning.

4. An articulated upper limb splint as claimed in claim 3 and comprising a shoulder sling, a first strap secured to one end of said sling for attaching said one end of said sling to the free end of said first trough, and a second strap secured to the other end of said sling for detachably connecting the other end of said sling to said adjustable strap securing the opposite ends of said hand grip to said second trough.

5. An articulated upper limb splint as claimed in claim 2 and comprising a shoulder sling, a first strap secured to one end of said sling for attaching said one end of said sling to the free end of said first trough, and a second strap secured to the other end of said sling for detachably connecting said other end of said sling to the free end of said first trough.

6. An upper limb splint according to claim 1 further comprising:
   (a) a hand grip; and
   (b) an adjustable strap secured to opposite ends of said hand grip and attached to said distal limb support section to enable said hand grip to be movable for adjustable positioning.

7. An upper limb support splint according to claim 6 further comprising:
   (a) a shoulder sling;
   (b) a first strap secured to one end of said sling for attaching one end of said sling to said proximal limb support section; and
   (c) a second strap releasably attached to said adjustable strap, wherein said adjustable strap is secured to the opposite ends of said hand grip for attaching said other end of said sling to said distal limb support section.

8. An upper limb support splint as claimed in claim 7 wherein said proximal limb support section includes a first trough which is engaged by a limb and wherein said distal limb support section includes a second trough which is engaged by the limb and wherein said first strap attached to one end of said sling is attached to said first trough of said proximal limb support section, and wherein said second strap secured to the opposite end of said sling is detachably connected to said adjustable strap which is secured to the opposite end of said sling, and wherein said adjustable strap which is secured to the opposite end of said sling is attached to said second trough.

9. An upper limb splint according to claim 1 further comprising a sling attached to said frame at the opposite ends thereof, said sling comprising a pad having a core of foam material enveloped by a closed cell material to inhibit the flow of foreign substances into said core of foam material.

10. An upper limb splint according to claim 1 further comprising a sling attached to said frame at the opposite ends thereof, said sling comprising a pad having a core of foam material enveloped by nylon to inhibit the flow of foreign substances into said core of foam material.

* * * * *